US005261902A

United States Patent [19]

Okada et al.

[11] Patent Number: 5,261,902

[45] Date of Patent: Nov. 16, 1993

[54] FLUID CONTAINER ASSEMBLY

[75] Inventors: Kiyonori Okada, Tokyo; Mitugu Inaba, Ibaraki; Seizo Sunago, Hyogo; Osamu Takahata, Osaka, all of Japan

[73] Assignee: Fujisawa Pharmaceutical Co., Ltd., Osaka, Japan

[21] Appl. No.: 889,257

[22] Filed: May 28, 1992

[30] Foreign Application Priority Data

May 29, 1991 [JP] Japan ................................ 3-126147
Apr. 30, 1992 [JP] Japan ................................ 4-111369

[51] Int. Cl.$^5$ ............................................ A61M 5/00

[52] U.S. Cl. .................................. 604/416; 604/403; 215/DIG. 3

[58] Field of Search .............. 604/416, 410, 411, 403; 206/219, 222; 215/227, 293, 295, 296, 355, DIG. 3

[56] References Cited

U.S. PATENT DOCUMENTS

D. 323,389 1/1992 Aoki et al. .
3,206,080 9/1985 Scislowicz .
4,432,755 2/1984 Pearson ................................ 604/56
4,484,920 11/1984 Kaufman et al. .................. 604/416
4,583,971 4/1986 Bocquet et al. .
4,589,879 5/1986 Pearson .............................. 604/411
4,932,937 6/1990 Gustavsson et al. ................ 604/87
4,936,841 6/1990 Aoki et al. .
4,950,237 8/1990 Henautt et al. ....................... 604/82
5,114,004 5/1992 Isono et al. ......................... 206/222

FOREIGN PATENT DOCUMENTS 0117489 9/1984 European Pat. Off. .
0155560 9/1985 European Pat. Off. .
2239390 2/1975 France .

*Primary Examiner*—Robert A. Hafer
*Assistant Examiner*—Sam Rimell
*Attorney, Agent, or Firm*—Oblon, Spivak, McClelland, Maier & Neustadt

[57] ABSTRACT

A fluid container assembly including a flexible vessel containing a solvent or diluent and having a fluid communicating port in an upper portion thereof, a drug container containing a drug and having a drug communicating port in a lower portion thereof, and a connecting part for connecting the fluid communicating port of the flexible vessel to the drug communicating port of the drug container, wherein the connecting part includes a plug removably fitted into both the fluid communicating port and the drug communicating port and a plug holding extendable member for holding the plug while unplugging the same when assuming its extended position, the member connecting the outer periphery of the fluid communicating port to the outer periphery of the drug communicating port and defining a fluid communicating path.

3 Claims, 8 Drawing Sheets

FLUID CONTAINER ASSEMBLY

BACKGROUND OF THE INVENTION

1. Field of the Invention

The present invention relates to a fluid container assembly, and more particularly to a fluid container assembly used for drip infusion.

2. Description of the Related Art

Hitherto, a drug in the form of powders or freeze-dried powders contained in a vessel such as a vial has been dissolved with a diluent and used as fluid for drip infusion in a medical organization such as a hospital. In that case, a vessel containing the drug is connected to a vessel containing a liquid for dissolving or diluting a drug by means of a connector such as a double-edged needle or communicating pipe. The liquid for dissolving or diluting a drug is moved into the vessel containing the drug to dissolve the drug therewith.

Such procedure is, however, complicated and time consuming. Moreover, there is a possibility of the drug in the vessel being contaminated because a hole for connection is formed on the vessel containing the drug in the open air.

In order to solve the above-mentioned problem, there has been proposed a fluid container as shown in Japanese Unexamined Patent Publication No. 501129/1986 (which corresponds to U.S. Pat. No. 4,583,971).

As shown in FIG. 12, the fluid container comprises a capsule (102) encasing a vial (101), i.e., a drug container, and a flexible vessel (103) containing a liquid for dissolving or diluting a drug and having a fluid outlet. The capsule (102) and flexible vessel (103) are connected to each other through a tube (104). In the tube (104), a hollow needle (105) is provided on the vial (101) side while a breaking member (106) is provided on the flexible vessel (103) side. The breaking member (106) closes a passage of the tube (104) and obstructs a flow of fluid.

In use, a cap (107) on the top of the capsule (102) is pushed with a finger to press down the vial (101). The needle (105) penetrates a rubber plug (108) of the vial (101) so that the flexible vessel (103) and the vial (101) are connected to each other. The breaking member (106) in the tube (104) is then bent with hands to open the passage of the tube (104) and to mix the drug and the liquid for dissolving or diluting a drug.

The above-mentioned fluid container is improved in the point that mixing procedure is performed by communicating a drug container to a flexible vessel containing a liquid for dissolving or diluting a drug. The mixing procedure is still troublesome because a passage must be opened by bending the breaking member (106) with hands after sticking the rubber plug (108) of the vial (101) with the needle (105). Moreover, when the bending of the breaking member (106) is incomplete, fluid is hard to pass through the tube so that it takes much time to carry out the dissolution of the drug. Furthermore, the number of parts is relatively large so that costs are increased.

SUMMARY OF THE INVENTION

The present invention was made to eliminate the above-mentioned drawbacks, and intends to provide a fluid container assembly enabling sure and easy communication between a drug container and a vessel of a liquid for dissolving or diluting a drug with a simple structure, and capable of shortening a time required for the mixing of the drug and the liquid for dissolving or diluting a drug at small costs.

The present invention provides a fluid container assembly comprising a flexible vessel containing a solvent or diluent and having a fluid communicating port in an upper portion thereof, a drug container containing a drug and having a drug communicating port in a lower portion thereof, and a connecting part for connecting the fluid communicating port of the flexible vessel to the drug communicating port of the drug container, wherein the connecting part comprises a plug removably fitted into both the fluid communicating port and the drug communicating port and a plug holding extendable member for holding the plug while unplugging the same when assuming its extended position, the member connecting the outer periphery of the fluid communicating port to the outer periphery of the drug communicating port and defining a fluid communicating path.

According to the present invention, the drug container is caused to separate from the flexible vessel in the opposite direction so as to unplug the plug which blocks the drug communicating port in the lower portion of the drug container (as shown in FIG. 1 or 6, or the neck portion of the drug container) and the fluid communicating port in the upper portion of the flexible vessel (as shown in FIG. 1 or 6). Consequently, the drug container is communicated to the flexible vessel. Thus, the drug is mixed with the liquid for dissolving or diluting a drug so that a drug solution can be prepared.

Communication between the drug container and flexible vessel is made by unplugging the plug from the communicating ports of the drug container and flexible vessel. Then, the drug is mixed with the liquid for dissolving or diluting a drug through the fluid communicating path formed between the plug holding extendable member and the plug. In brief, if the drug container and flexible vessel are pulled or relatively rotated so as to separate from each other in the opposite directions, the drug solution can surely be prepared.

According to the present invention, the plug can be made of a rubber, a plastic or the like, preferably a rubber.

Examples of the plug holding extendable member include a bellows tube as a pull type member and the combination of cylinders having grooves and projections as a rotary type member.

DESCRIPTION OF THE PREFERRED EMBODIMENTS

Preferred embodiments of the present invention will be described in detail with reference to the drawings. The present invention should not be construed as being limited by the following embodiments.

Figure 1:
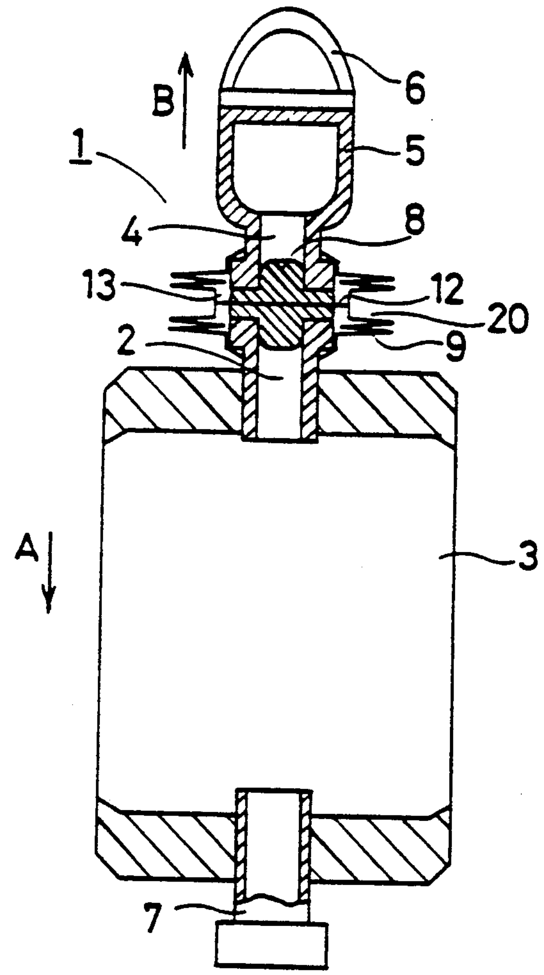
FIG. 1 is a longitudinal section view showing an embodiment according to the present invention.

FIG. 1 shows a fluid container assembly using a plug holding extendable member of a pull type.

In FIG. 1, a fluid container (1) comprises a flexible vessel (hereinafter referred to as a bag) (3), a drug vial (hereinafter referred to as a vial) (5) as a drug container, and a connecting part (20). The bag (3) contains a liquid for dissolving or diluting a drug therein in a sterilizing condition and has a fluid communicating port (2) in an upper portion thereof. The vial (5) contains a solid drug therein in an aseptic condition and has a drug communicating port (4) in a lower portion thereof. The connecting part (20) connects the fluid communicating port (2) to the drug communicating port (4). The reference numeral (6) denotes a suspension member which is provided on the top of the vial (5) and is made of a soft polypropylene resin or the like. The reference numeral (7) denotes a fluid outlet which is provided in the lower portion of the bag (3).

The bag (3) is made of a flexible material such as a soft vinyl chloride resin, a polyolefine resin, an ethylene vinyl acetate copolymer, or the like. It is preferred that the bag (3) is made of a polyolefine resin which has good chemical resistance and is eluted little.

Examples of the liquid for dissolving or diluting a drug contained in the bag (3) include a physiological saline solution, a 5% glucose solution, distilled water for infusion, a solution containing various electrolytes, and the like.

The vial (5) (container body) is made of a known glass or plastic, and contains a solid drug therein.

Examples of a drug contained in the vial (5) include an antibiotics, an antitumor agent, an antiulcer agent and the like.

As an antibiotics, there can be used cephem antibiotics such as cefazolin sodium, ceftizoxime sodium, cefotiam dihydrochloride, cefmenoxime hemihydrochloride, cefacetrile sodium, cefamandole sodium, cefaloridine, cefotaxime sodium, cefotetan sodium, cefoperazone sodium, cefsulodin sodium, ceftezole sodium, cefpiramide sodium, cefmetazole sodium, or cefuroxime sodium; or penicillin antibiotics such as ampicillin sodium, carbenicillin disodium, sulbenicillin disodium, or ticarcillin sodium. As an antitumor agent, mitomycin C, fluorouracil, tegafur, cytarabine, etc. can be used. As an antiulcer agent, famotidine, ranitidine hydrochloride, cimetidine, etc. can be used.

Figure 3:
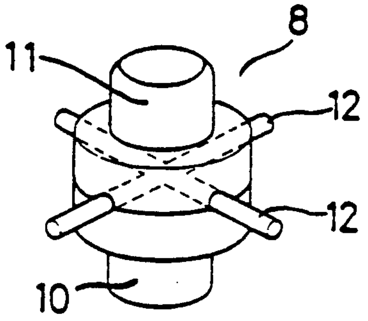
FIG. 3 is a perspective view of a rubber plug according to the embodiment.

The connecting part (20) includes an integral rubber plug (8) and a bellows tube (9). The rubber plug (8) is removably fitted into the fluid communicating port (2) and the drug communicating port (4). The bellows tube (9) is made of a soft plastic, and serves as a plug holding movable member for connecting the outer periphery of the fluid communicating port (2) to that of the drug communicating port (4) and for supporting the rubber plug (8) therein. As shown in FIG. 3, the rubber plug (8) has lower and upper portions (10) and (11) integrally bonded back to back through an intersecting portion (12). The lower portion (10) is fitted into the fluid communicating port (2). The upper portion (11) is fitted into the drug communicating port (4). The intersecting portion (12) is made of a soft plastic. Each tip end of the intersecting portion (12) is supported integrally with an inner wall on the center of the bellows tube (9) by bonding or fusion. A fluid communicating path (13) is provided between the bellows tube (9) and the rubber plug (8).

There will be described a method for using the fluid container assembly (1) having the above-mentioned structure.

Figure 2:
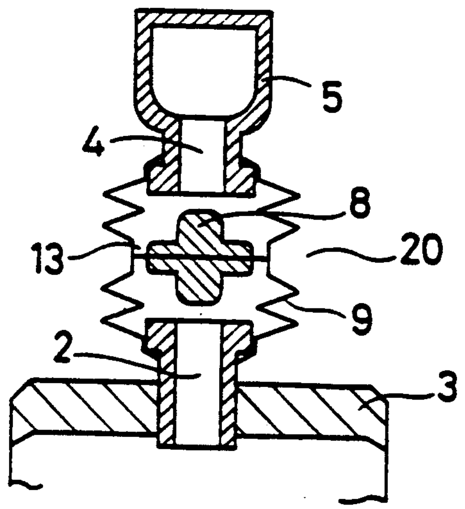
FIG. 2 is a longitudinal section view of a main part showing the state of use according to the embodiment.

In FIGS. 1 and 2, when the bag (3) and the vial (5) are pulled in the opposite directions (shown by arrows A and B), the rubber plug (8) can be unplugged from the fluid communicating port (2) and drug communicating port (4). Consequently, the bag (3) can be communicated to the vial (5) through the fluid communicating port (2), drug communicating port (4) and fluid communicating path (13).

When the bag (3) is intermittently compressed or the fluid container (1) is turned upside down, the liquid for dissolving or diluting a drug in the bag (3) goes to and from the vial (5) to dissolve the drug contained in the vial (5). Consequently, a drug solution can uniformly be prepared in the fluid container assembly (1).

Figure 4:
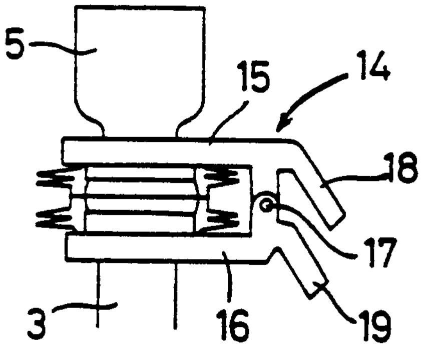
FIG. 4 is side view of a main part showing the state where a clamp is attached
Figure 5:
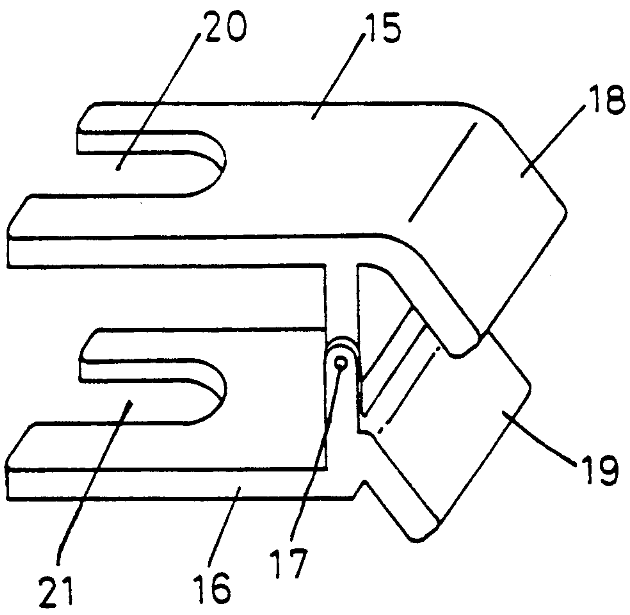
FIG. 5 is a perspective view of the clamp

Before use, the outside of the bellows tube (9) may be held by a clamp (14) as shown in FIG. 4 such that the rubber plug (8) is not unplugged from the communicating ports (2) and (4). In FIGS. 4 and 5, the clamp (14) has such a structure that upper and lower fragments (15) and (16) are urged by a shaft (17) and a spring (not shown) in the holding direction. By fitting U-shaped portions (20) and (21) of the upper and lower fragments (15) and (16) in the neck portions (flange portions) of the vial (5) and bag (3) as shown in FIG. 4, the bellows tube (9) can be prevented from extending. The reference numerals (18) and (19) denote handle portions of the clamp (14).

Figure 6:
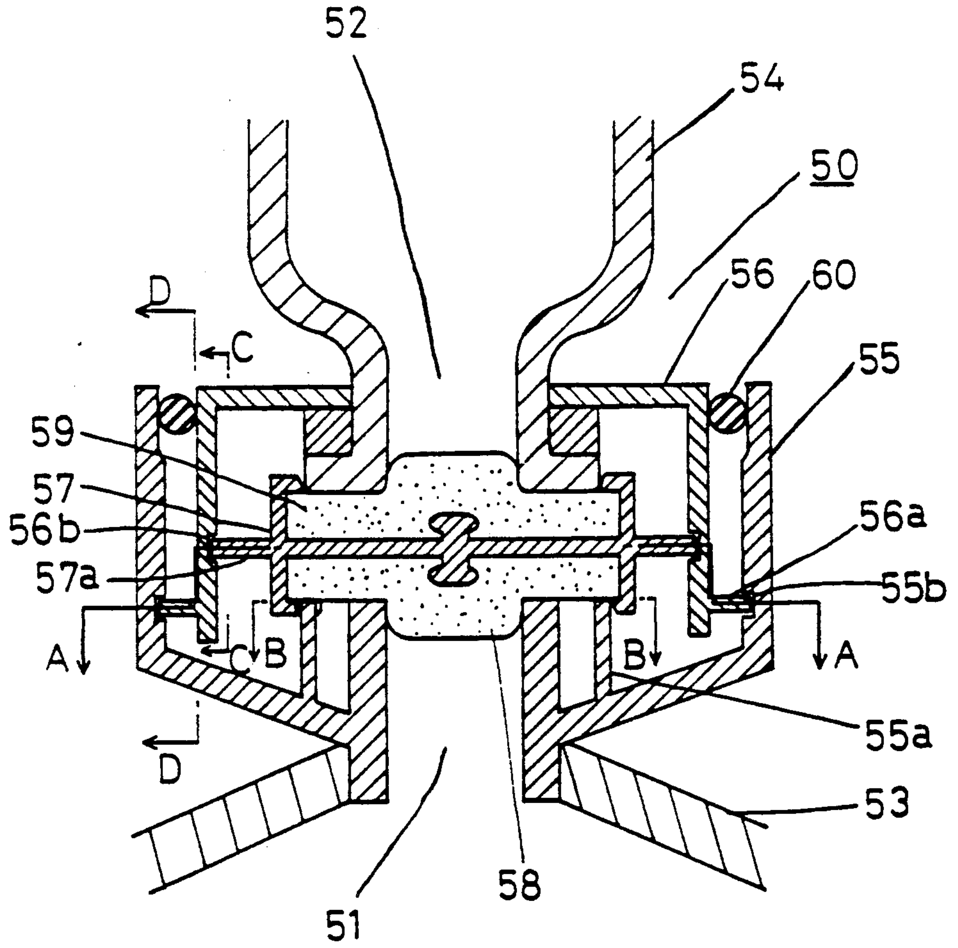
FIG. 6 is a longitudinal section view of a connecting part according to another embodiment of the present invention.

FIG. 6 shows a connecting part of a fluid container assembly using a plug holding extendable member of a rotary type as another embodiment of the present invention.

In FIG. 6, a connecting part (50) includes a bag plug (58), a vial plug (59), a plug holding member (57), an inner cylinder (56), an outer cylinder (55) and a packing (60). The bag plug (58) and vial plug (59) are removably fitted into a fluid communicating port (51) of a bag (53) and a drug communicating port (52) of a vial (54), respectively. The plug holding member (57) integrally holds the bag plug (58) and the vial plug (59). The inner cylinder (56) is fixed to the outer periphery of the drug communicating port (52). The outer cylinder (55) is fixed to the outer periphery of the fluid communicating port (51). The packing (60) is fixed to the outer cylinder (55) for sealing the inside of the connecting part (50).

Four projections (56*a*) are provided on the outer periphery of the inner cylinder (56) and are fitted into grooves (55*b*). The grooves (55*b*) are provided on the inner periphery of the outer cylinder (55).

Four projections (57*a*) are provided on the outer periphery of the plug holding member (57) and are fitted into grooves (56*b*). The grooves (56*b*) are provided on the inner periphery of the inner cylinder (56).

The reference numeral (55*a*) denotes a stopper for preventing the plug holding member (57) from rotating. Two stoppers (55*a*) are provided.

Figure 8:
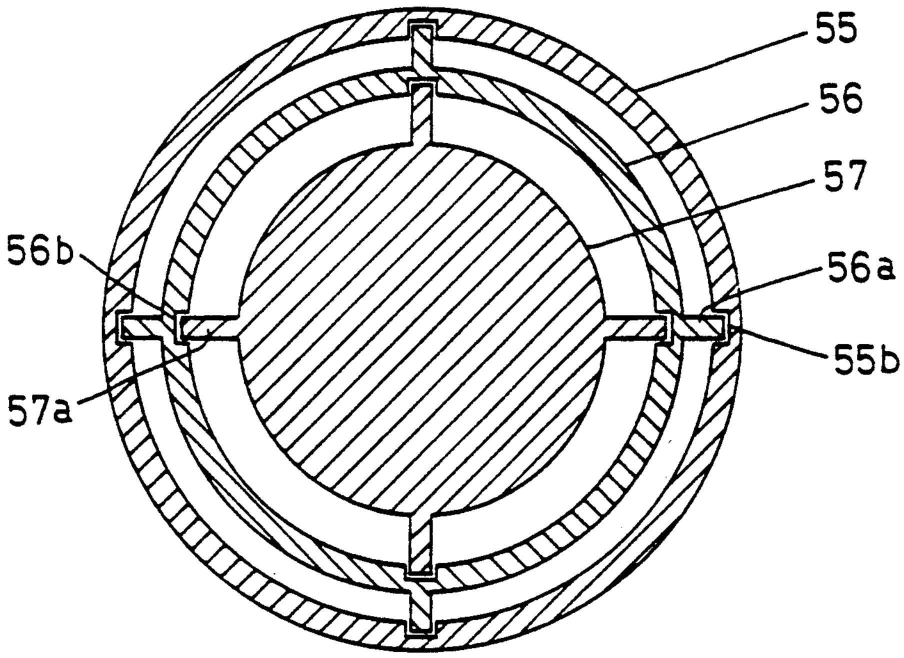
FIG. 8 is a section view taken along the line A—A shown in FIG. 6.

FIG. 8 is a section view taken along the line A—A in FIG. 6, and shows the relationships between the groove (55*b*) and the projection (56*a*) and between the groove (56*b*) and the projection (57*a*).

Figure 9:
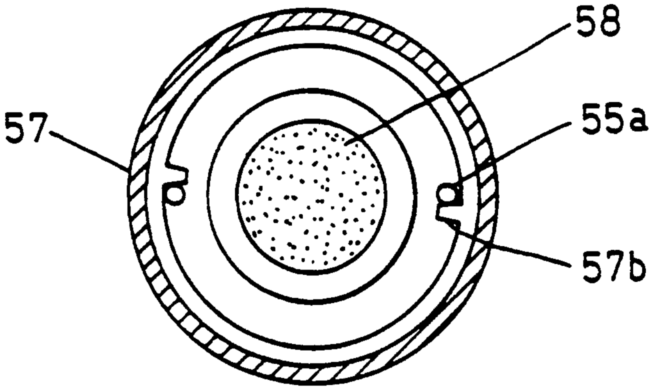
FIG. 9 is a section view taken along the line B—B shown in FIG. 6.

FIG. 9 is a section view taken along the line B—B in FIG. 6, and shows the relationship between the stopper (55*a*) and the projection (57*b*). As apparent from FIG. 9, the plug holding member (57) does not rotate counterclockwise because the projection (57*b*) is in contact with the stopper (55*a*).

Figure 10:
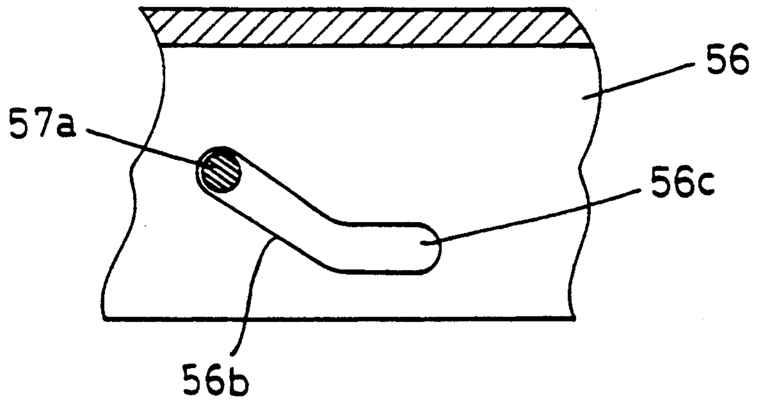
FIG. 10 is a section view taken along the line C—C shown in FIG. 6.

FIG. 10 is a section view taken along the line C—C in FIG. 6, and shows the shape of the groove (56*b*).

Figure 11:
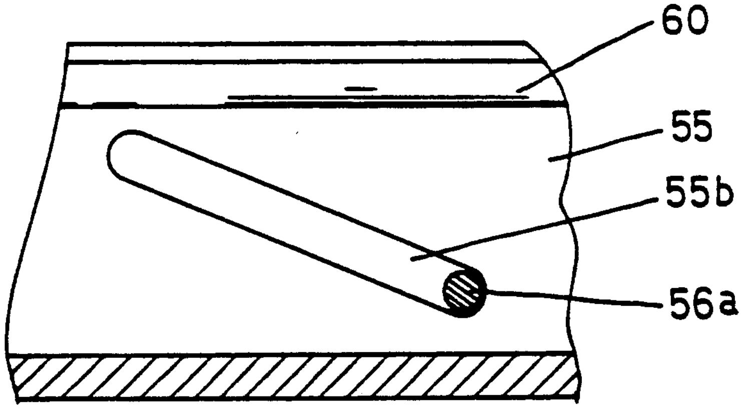
FIG. 11 is a section view taken along the line D—D shown in FIG. 6.
Figure 12:
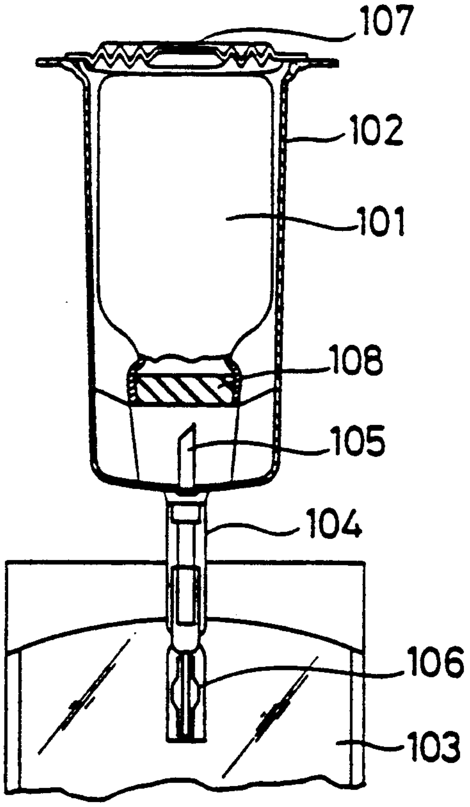
FIG. 12 (PRIOR ART)
FIG. 12 is a partially sectional front view according to the prior art.

FIG. 11 is a section view taken along the line D—D in FIG. 6, and shows the shape of the groove (55*b*).

There will be described a method for using the fluid container assembly provided with the connecting part (50) having the above-mentioned structure.

In FIG. 6, the outer cylinder (55) is fixed and the vial (54) is rotated counterclockwise when seen from above. As apparent from FIG. 11, the projection (56*a*) of the inner cylinder (56) ascends the groove (55*b*) so that the vial (54) is raised. As shown in FIG. 9, however, the stopper (55*a*) prevents the plug holding member (57) from rotating. As apparent from FIG. 10, even if the inner cylinder (56) ascends while rotating, the projection (57*a*) of the plug holding member (57) is not moved. Consequently, the plug holding member (57), bag plug (58) and vial plug (59) remain stationary. Accordingly, the vial (54) and the inner cylinder (56) are raised so that the vial plug (59) is unplugged from the drug communicating port (52) first.

Further, when the vial (54) is rotated counterclockwise, the projection (56*a*) of the inner cylinder (56) further ascends the groove (55*b*) as seen from FIG. 11. Consequently, the inner cylinder (56) is raised together with the vial (54). As a result, a horizontal groove portion (56*c*) is fitted into the stationary projection (57*a*) shown in FIG. 10. The horizontal groove portion (56*c*) is provided on the lower right of the groove (56*b*). Furthermore, since the inner cylinder (56) is raised, the horizontal groove portion (56*c*) of the groove (56*b*) lifts up the projection (57*a*). Consequently, the plug holding member (57) formed integrally with the projection (57*a*) is raised together with the bag plug (58). Thus, the bag plug (58) is unplugged from the fluid communicating port (51).

Figure 7:
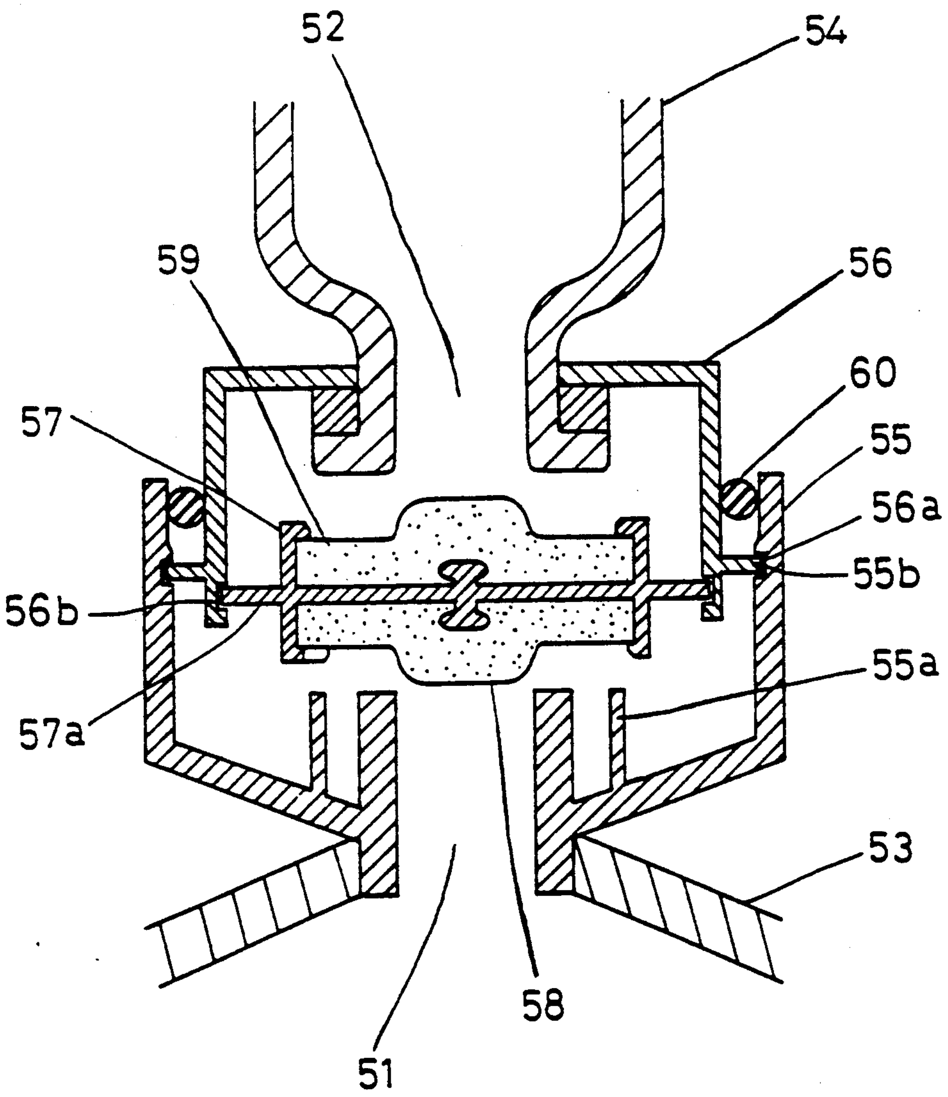
FIG. 7 is a longitudinal section view showing the state where the connecting part in FIG. 6 is used.

More specifically, when the vial (54) is rotated counterclockwise, it can be communicated to the bag (53). This state is shown in FIG. 7.

While four projections (56*a*) and four projections (57*a*) are provided in the above-mentioned embodiment, three projections (56*a*) and three projections (57*a*) may be used.

According to the fluid container assembly (1) described above, the number of parts can be decreased, and a drug solution can easily be prepared by pulling or rotating the vial (5) or (54) and the bag (3) or (53). When the rubber plug (8) [bag plug (58) and vial plug (59)] is unplugged from the drug communicating port (4) or (52) and the fluid communicating port (2) or (51), a drug can come in contact with a liquid for dissolving or diluting a drug through a preformed fluid communicating path and a fluid communicating path which is newly formed by unplugging the plug. Consequently, the drug solution can surely be prepared.

According to the present invention, a flexible vessel can be communicated to a drug container very surely and easily. Furthermore, the number of parts can be decreased so that costs can be reduced.

What we claim is:

1. A fluid container assembly comprising a flexible vessel containing a solvent or diluent and having a fluid communicating port in an upper portion thereof, a drug container containing a drug and having a drug communicating port in a lower portion thereof, and a connecting part for connecting the fluid communicating port of the flexible vessel to the drug communicating port of the drug container, wherein said connecting part includes a plug mounted therein, said connecting part having a first position wherein said plug is fitted into both the fluid communicating port and the drug communicating port, and said connecting part having an extended position wherein said vessel and said drug container are separated from one another such that said plug is disengaged from both said fluid connecting port and said drug connecting port, said connecting part connecting the outer periphery of the fluid communicating port to the outer periphery of the drug communicating port and defining a fluid communicating path.

2. A fluid container assembly as set forth in claim 1, wherein said connecting part includes a plug holding extendable member made of a bellows.

3. A fluid container assembly comprising a flexible vessel containing a solvent or diluent and having a fluid communicating port in an upper portion thereof, a drug container containing a drug and having a drug communicating port in a lower portion thereof, and a connecting part for connecting the fluid communicating port of the flexible vessel to the drug communicating port of the drug container, wherein said connecting part comprises a plug removably fitted in both the fluid communicating port and the drug communicating port and a plug holding extendable member for holding the plug while unplugging the same when assuming its extended position, said member connecting the outer periphery of the fluid communicating port to the outer periphery of the drug communicating port and defining a fluid communication path, wherein said plug holding extendable member has an inner cylinder fixed to the outer periphery of the drug communicating port and formed with a projection at an outer circumferential surface thereof, an outer cylinder fixed to the outer periphery of the fluid communicating port and formed with a groove in an inner circumferential surface thereof, and a packing fixed to the outer cylinder for sealing inside of the connecting part, said projection of the inner cylinder being engaged with the groove of the outer cylinder.

* * * * *